United States Patent [19]

Knighton

[11] 4,300,572
[45] Nov. 17, 1981

[54] FLUID ADMINISTERING AND PRESSURE SENSING APPARATUS

[76] Inventor: David R. Knighton, 80 Southwood Dr., San Francisco, Calif. 94112

[21] Appl. No.: 103,373

[22] Filed: Dec. 13, 1979

[51] Int. Cl.³ .......................... A61M 5/14; A61B 5/02
[52] U.S. Cl. .................................... 128/674; 128/673; 128/214 E; 128/214 R
[58] Field of Search ............... 128/674, 214 R, 214.2, 128/214 E, 673

[56] References Cited

U.S. PATENT DOCUMENTS

| | | | |
|---|---|---|---|
| 3,124,133 | 3/1964 | Marbach | 128/674 |
| 3,610,230 | 10/1971 | Anderson | 128/674 |
| 3,844,283 | 10/1974 | Dabney | 128/214 |
| 3,934,576 | 1/1976 | Danielsson | 128/214 |

*Primary Examiner*—Robert W. Michell
*Assistant Examiner*—Nancy A. B. Swisher
*Attorney, Agent, or Firm*—Robert Charles Hill

[57] ABSTRACT

An apparatus for selectively measuring central venous pressure and effecting hyperalimentation through a single catheter inserted into a central vein of the patient. The apparatus includes a manometer, a first selector valve connected to an upper portion of the manometer tube, a hyperalimentation fluid supply connected to the valve, a sterile air supply connected to the valve, a second selector valve connected to a lower end portion of the manometer tube, a waste container connected to the second selector valve, and a catheter connected to the second selector valve. The first selector valve is arranged to connect alternatively the hyperalimentation fluid supply or the sterile air supply to the upper end portion of the manometer tube, and the second selector valve is arranged to connect alternatively the lower end portion of the manometer tube selectively to the waste container or the catheter. A check valve may be connected between the waste container and the second selector valve and an isolation valve may be connected between the catheter and the second selector valve. A lock is provided for locking the catheter to the connection to the second selector valve. The selector valves in the illustrated embodiment are defined by two-way stopcocks. The apparatus is completely closed at all times relative to the ambient atmosphere.

9 Claims, 2 Drawing Figures

FLUID ADMINISTERING AND PRESSURE SENSING APPARATUS

BACKGROUND OF THE INVENTION

1. Field of the Invention

This invention relates to medical devices and in particular to apparatus for selectively measuring central venous pressure and effecting hyperalimentation of a patient.

2. Description of the Prior Art

In connection with patients requiring administration of parenteral fluids, it is often highly desirable to obtain a measurement of the central venous pressure of the patient so as to advise the clinician as to the fluid and blood status. The central venous pressure provides an indication of the fluid pressure at the right side of the heart. Examples of such patients include those who have undergone major trauma, major operations, septic patients, or patients who have possibility of fluid shifts. In such patients, it is important to continuously provide information as to the central venous pressure to the clinician.

Normally, the central venous pressure is measured by inserting a catheter through a peripheral vein into the right heart portion, or superior vena cava. A problem arises, however, in the conventional technique for effecting such central venous pressure measurement in that the techniques require the opening of a column of fluid to the atmosphere which destroys the complete sterility thereof.

Another problem in the conventional techniques for measuring central venous pressure is that in the techniques wherein the pressure is determined by a fluid manometer sensor, blood in the sensor may reflux and return through the connection to the patient, again providing a possibility of contamination.

It is common to utilize such central venous pressure determinations in connection with parenteral fluid administration. Illustratively, such sensing is utilized in connection with hyperalimentation, i.e. total parenteral nutrition, fluid administration. In such administration, large amounts of calories and proteins may be given to a patient so as to provide all necessary nutrients for growth, survival and healing. Such parenteral fluid administration is conventionally effected by means of a catheter placement similar to that used in the central venous pressure determinations. However, in connection with such parenteral fluid administration, the problem of sterility is of maximum importance as normally relatively high concentrations of glucose are utilized in such parenteral fluid administrations. Such high levels of glucose provide an ideal medium for bacterial growth and, thus, aggravate the sterility problem.

It is further desirable in such medical treatment to minimize the number of catheter insertions. Still further, it is desirable to effect the central venous pressure determinations concurrently with the administration of the parenteral fluids for optimum surveillance of the patient's conditions. Conventionally, two separate catheters have been employed from two separate sites in the superior vena cava vein to provide such concurrent pressure determination and parenteral fluid administration.

It is well known that insertion of such catheters has a morbidity factor of between approximately 0.2% to 0.5%. Further, the requirement of multiple catheter insertions limits the available venous access site.

A number of prior art patents have been directed to the use of manometers and parenteral fluid administration techniques. Illustratively, U.S. Pat. No. 3,242,920 of H. W. Andersen shows a manometer for measuring venous pressure and including an intravenous infusion supply connected to the manometer tube through a "T" connector.

Paul E. Rockwell, in U.S. Pat. No. 3,413,970 shows means for measuring central venous pressure utilizing a manometer with the manometer and a parenteral fluid supply being connected to the catheter inserted into the patient through a three-way valve.

In U.S. Pat. No. 3,590,818, Gerald T. Lemole shows a device having correlated manometer and intravenous fluid supply means wherein a three-way stopcock separately and at various times places the intravenous fluid against the manometer fluid, the intravenous fluid from the patient's veins against the manometer fluid, and provides intravenous fluid from the source to the vein.

Saul Leibinsohn, in U.S. Pat. No. 3,690,312, shows a venous pressure manometric device with level magnifying means wherein a stopcock interconnects a plurality of the fluid carrying ducts of the system. In taking the venous pressure with the Leibinsohn device, sterile isosmotic water is allowed to run into the reservoir tube by suitable positioning of the stopcock rotatable plug. Subsequently, the plug is again rotated to allow the water to flow by gravity into the patient. A bag is secured to the upper end of the manometer tube for expansively closing the tube.

Curt Danielsson, in U.S. Pat. No. 3,934,576, shows a system including a multiway valve for selectively connecting pressure measuring means and fluid supply means to the catheter inserted into the patient. The catheter may comprise a valved catheter. Luer-Lok connecting means may be utilized at different portions of the system.

SUMMARY OF THE INVENTION

The present invention comprehends an improved apparatus and system for selectively measuring central venous pressure and effecting hyperalimentation of a patient through a single catheter inserted into a central vein of the patient.

The apparatus of the illustrated embodiment includes a manometer having a vertical measuring tube defining an upper end portion and a lower end portion, a first selector valve connected to the upper end portion of the manometer tube, means for connecting a hyperalimentation fluid supply to the valve, means for connecting a sterile air supply to the valve, the valve being arranged to connect alternatively (a) the hyperalimentation fluid supply or (b) the sterile air supply to the upper end portion of the manometer tube, a second selector valve connected to the lower end portion of the manometer tube, means for connecting a waste container to the second selector valve, and means for connecting a catheter to the second selector valve, the second selector valve being arranged to connect alternatively the lower end portion of the amnometer tube to (c) the waste container or (d) the catheter.

In the illustrated embodiment, a check valve is connected between the waste container and the second selector valve for preventing fluid flow reversely from the waste container into the second selector valve.

In the illustrated embodiment, an isolation valve is connected to the means for connecting the catheter to the second selector valve.

Further, in the illustrated embodiment, lock means are provided for locking the catheter to the means connecting the catheter to the second selector valve.

In the illustrated embodiment, the selector valves comprise two-way stopcocks.

In the illustrated embodiment, the sterile air supply is defined by a flexible bag.

BRIEF DESCRIPTION OF THE DRAWING

Other features and advantages of the invention will be apparent from the following description taken in connection with the accompanying drawing wherein.

DESCRIPTION OF THE PREFERRED EMBODIMENT

Figure 1:
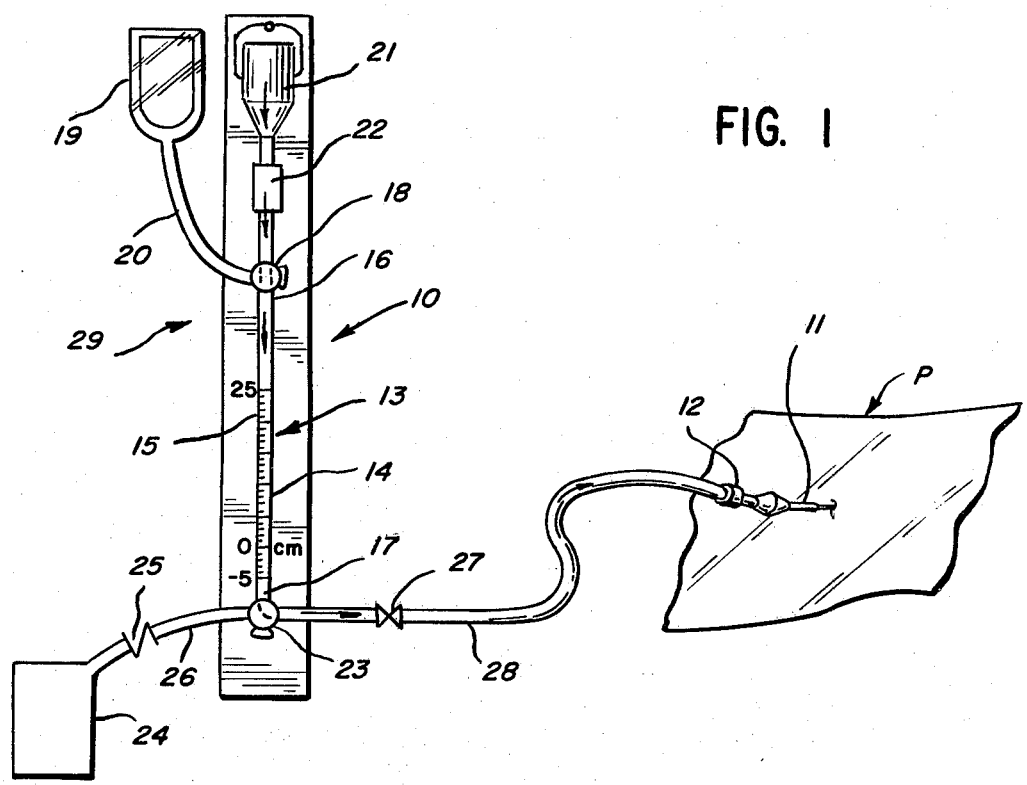
FIG. 1 is a fragmentary elevational view illustrating the use of an apparatus embodying the invention in administering the parenteral fluid through a catheter to a patient.

In the exemplary embodiment of the invention as disclosed in the drawing, an apparatus generally designated 10 is shown to comprise an apparatus for selectively measuring central venous pressure and effecting hyperalimentation of a patient P through a catheter 11 connecting through a peripheral vein to the superior vena cava of the patient. As shown in FIG. 1, catheter 11 may be provided with a Luer-Lok connector 12.

Apparatus 10 includes a manometer generally designated 13 defined by a vertical tube 14 having suitable scale markings 15 for indicating the central venous pressure when the tube is placed in fluid pressure communication with the patient's vena cava through the catheter 11.

Tube 14 defines an upper end portion 16 and a lower end portion 17. A first two-way stopcock selector valve 18 is connected to the upper portion 16 of the manometer tube for selectively connecting a sterile air supply 19 through a tube 20 to the manometer tube portion 16 or a parenteral fluid supply 21 through a dripmeter 22 to the manometer upper end portion 16.

A second two-way stopcock selector valve 23 is connected to the lower end portion 17 of the manometer tube 14. A waste container 24 is connected through a check valve 25 in a connecting duct 26 to the second valve 23 and the second valve is further connected through an isolation valve 27 in a delivery duct 28 to the catheter 11 by means of the Luer-Lok connection 12.

As can be seen in FIG. 1, the system generally designated 29 is completely closed so as to avoid the possibility of contamination as from airborne bacteria, etc. The system is further arranged so as to prevent return of the patient's blood from the waste container 24, further preventing possible contamination. The Luer-Lok connection 12 effectively positively retains the apparatus in association with the inserted catheter 11, further preventing possible contamination during the continuous use of the system.

As discussed above, the use of the system in providing the desired total parenteral nutrition fluid administration to the patient is illustrated in FIG. 1. Thus, in effecting this operation, stopcock 16 is arranged to provide communication from the fluid supply 21 while closing off the connection to the sterile air supply 19. At the same time, the stopcock 23 is arranged to provide communication from the lower portion 17 of the tube 14 through the duct 28 to the catheter 11. Under these conditions, parenteral fluid is delivered from the supply 21 to the patient's venous system as desired by the clinician.

Figure 2:
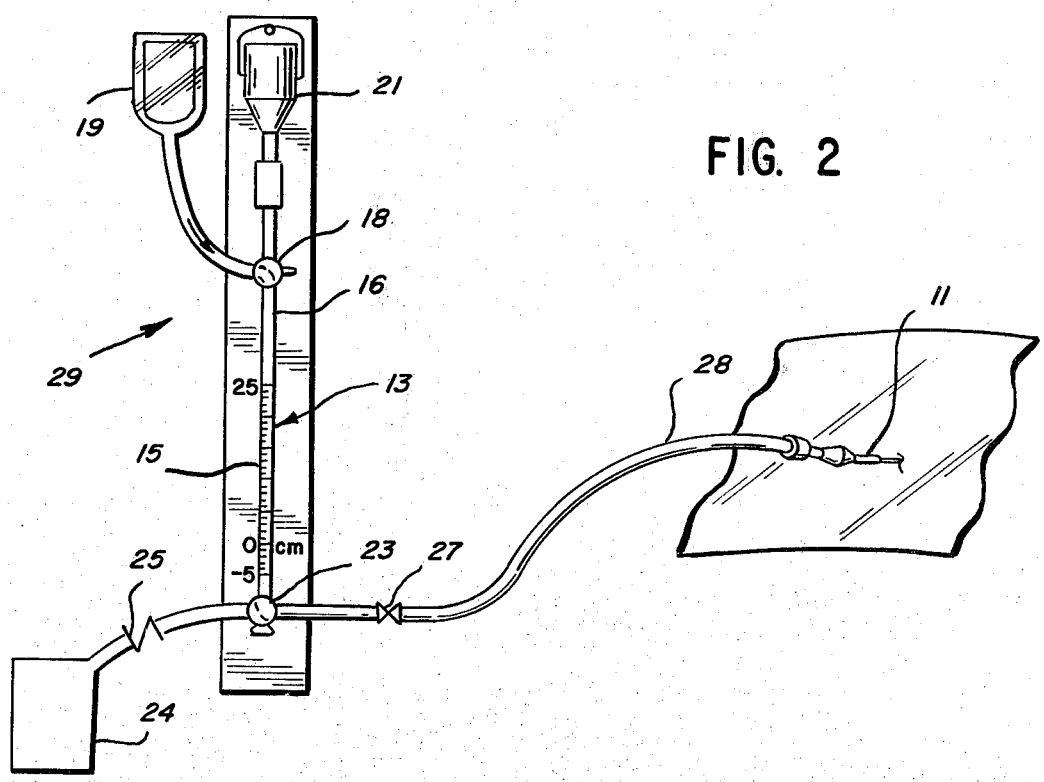
FIG. 2 is a similar view illustrating a rearrangement of the apparatus to provide a central venous pressure determination.

As further discussed above, it is desirable to regularly provide to the clinician information as to the central venous pressure. For this purpose, the apparatus may be readily rearranged in the arrangement of FIG. 2 by suitably adjusting the stopcock valves 18 and 23, as shown in FIG. 2, to connect the upper end portion 16 of the manometer tube to the sterile air supply 19 and close the connection through valve 18 to the parenteral fluid supply 21. Under these conditions, the central venous fluid pressure may be read against the scale 15 of manometer 13. It should be noted that such pressure determination is effected without any reconnection of the duct 28 to the catheter 11 or to a different catheter with the system 29 being maintained completely closed at all times relative to the ambient atmosphere, thereby assuring maintained sterility in the system.

Transfer of air and/or hyperalimentation fluids to the waste container 24 after each pressure measurement is maintained unidirectional by means of the check valve 25 which effectively prevents any reverse flow thereof back into the system.

Apparatus 10 provides substantial improved safety in the fluid administration and sensing operation as a result of the arrangement which assures that the blood effectively never leaves the patient notwithstanding the pressure determinations from time to time. The hyperalimentation fluid provides a sufficient fluid pressure in the system to cause the fluid flow through line 28 to be effectively outwardly only, notwithstanding the use of the bidirectional valve 27.

To prevent transfer of air to the patient subsequent to a pressure determination operation, any air which may pass into the hyperalimentation fluid during the sensing operation is transferred to the waste container 24 before reconnection of the system to the patient. More specifically, upon completion of the venous pressure determination, valve 27 is closed and the valve 23 is turned to place the lower end of tube 15 in communication with the waste container 24 through check valve 25.

Valve 18 is then turned to connect tube 15 to the supply 21, permitting the fluid to pass downwardly and flush from tube 15 any air remaining therein to the waste container 24. The elimination of this air may be visually determined by the user observing the condition of the fluid in tube 15 during the flushing operation. Upon elimination of all air from the fluid in tube 15, valve 23 is returned to the position of FIG. 1 and valve 27 is opened to re-establish the fluid administration arrangement of FIG. 1.

By permitting the use of a single catheter in connection with the maintained closed system which provides selectively parenteral fluid administration and central venous pressure determination, improved safety in the patient's care is obtained.

While, as will be obvious to those skilled in the art, other parameters may be utilized, in the illustrated embodiment, the parenteral fluid supply 21 may comprise a one liter supply, the sterile air container 19 may comprise a 200-cc. capacity bag formed of a suitable synthetic resin or the like, and the waste container may have a capacity of approximately 400 cc. As is well known in the art, the connection to the fluid supply may be effected by a piercing needle or similar connecting means associated with the drip meter 22 for piercing the normal closure membrane of the fluid supply container 21 and providing the desired fluid communication between the supply bottle and the administration system.

The foregoing disclosure of specific embodiments is illustrative of the broad inventive concepts comprehended by the invention.

I claim:

1. A completely closed system for selectively measuring central venous pressure and effecting hyperalimentation of a patient through a single catheter inserted into a vein of the patient, said apparatus comprising:
   a manometer having a vertical measuring tube defining an upper end portion and a lower end portion;
   a first selector valve connected to said upper end portion of the manometer tube;
   a hyperalimentation fluid supply;
   means for connecting said hyperalimentation fluid supply to said valve;
   a sterile air supply;
   means for connecting said sterile air supply to said valve, said valve being arranged to connect alternatively (a) said hyperalimentation fluid supply or (b) said sterile air supply to said upper end portion of the manometer tube;
   a second selector valve connected to said lower end portion of the manometer tube;
   a waste container;
   means for connecting said waste container to said second selector valve; and
   means for connecting said catheter to said second selector valve, said second selector valve being arranged to connect alternatively said lower end portion of the manometer tube to (a) the waste container or (b) said catheter.

2. The system of claim 1 further including a check valve connected between said second selector valve and said waste container.

3. The system of claim 1 further including an isolation valve connected between said catheter and said second selector valve.

4. The system of claim 1 further including an isolation valve connected between said catheter and said second selector valve, and lock means for releasably locking the connection of the catheter to the isolation valve.

5. A method within a closed system of selectively measuring central venous pressure and effecting hyperalimentation of a patient through a single catheter inserted into a vein of the patient, said method comprising the steps of:
   providing a manometer;
   providing a hyperalimentation fluid supply;
   providing a sterile air supply;
   providing a waste container;
   alternatively connecting (a) the hyperalimentation fluid supply or (b) the sterile air supply to an upper end portion of the manometer; and
   alternatively connecting the catheter or the waste container to a lower portion of the manometer, (a) said hyperalimentation fluid supply and catheter being concurrently connected to the manometer with the connection of the sterile air supply and waste container thereto being closed to effect a delivery of the hyperalimentation fluid to the patient, (b) said sterile air supply and catheter being concurrently connected to the manometer with the connection of the hyperalimentation fluid supply and waste container being closed to effect a venous pressure measurement, and (c) said hyperalimentation fluid supply and waste container being concurrently connected to the manometer with the connection of the sterile air supply and catheter being closed to flush out air from the fluid in the manometer after effecting a venous pressure measurement.

6. The method of selectively measuring central venous pressure and effecting hyperalimentation of a patient of claim 5 wherein blood from the patient is prevented from passing from said catheter to said manometer at all times.

7. The method of selectively measuring central venous pressure and effecting hyperalimentation of a patient of claim 5 wherein a two-way selector valve is provided for connecting said sterile air supply and hyperalimentation fluid supply alternatively to said manometer.

8. The method of selectively measuring central venous pressure and effecting hyperalimentation of a patient of claim 5 wherein a two-way selector valve is provided for connecting said waste container and catheter alternatively to said manometer.

9. The method of selectively measuring central venous pressure and effecting hyperalimentation of a patient of claim 5 wherein a two-way selector valve is provided for connecting said waste container and catheter alternatively to said manometer, the connection between the two-way valve and said catheter being closed during the flushing out of air in arrangement (c).

* * * * *